(12) United States Patent
Okada

(10) Patent No.: US 6,261,824 B1
(45) Date of Patent: Jul. 17, 2001

(54) GRAM NEGATIVE COCCOID BACTERIUM *OKADAELLA GASTROCOCCUS*

(76) Inventor: Takayuki Okada, Silverton Place, Level 6, Suite 64, Wickham Terrace, Brisbane, QLD 4000 (AU)

( * ) Notice: Subject to any disclaimer, the term of this patent is extended or adjusted under 35 U.S.C. 154(b) by 0 days.

(21) Appl. No.: 09/509,067
(22) PCT Filed: Sep. 22, 1998
(86) PCT No.: PCT/AU98/00791
  § 371 Date: Jul. 21, 2000
  § 102(e) Date: Jul. 21, 2000
(87) PCT Pub. No.: WO99/16861
  PCT Pub. Date: Apr. 8, 1999

(30) Foreign Application Priority Data

Sep. 22, 1997 (AU) .................................................. P09346

(51) Int. Cl.[7] .................................................. C12N 1/00
(52) U.S. Cl. .................... 435/243; 435/4; 435/7.32; 435/29; 435/34; 435/252.1
(58) Field of Search ................................ 435/243, 252.1, 435/4, 29, 34, 7.32

(56) References Cited

U.S. PATENT DOCUMENTS 5,464,755 * 11/1995 Bochner .

OTHER PUBLICATIONS

International Search Report for PCT/AU98/00791 dated Oct. 20, 1998.
International Preliminary Examination Report for PCT/AU98/00791 dated Jul. 26, 1999.
"Gram–Negative Aerobic/Microaerophilic Rods and Cocci", Bergey's Manual of Derteminative Bacteriology–9, pp. 71–102.
"Anaerobic Gram–Negative Cocci", Bergey's Manual of Determinative Bacteriology–9, pp. 347–348.

* cited by examiner

*Primary Examiner*—Leon B. Lankford, Jr.
(74) *Attorney, Agent, or Firm*—Marshall, O'Toole, Gerstein, Murray & Borun

(57) ABSTRACT

A new gram negative coccoid bacterium, *Okadaella gastrococcus* is disclosed. The bacterium was isolated from an animal with a gastrointestinal disorder.

9 Claims, 3 Drawing Sheets

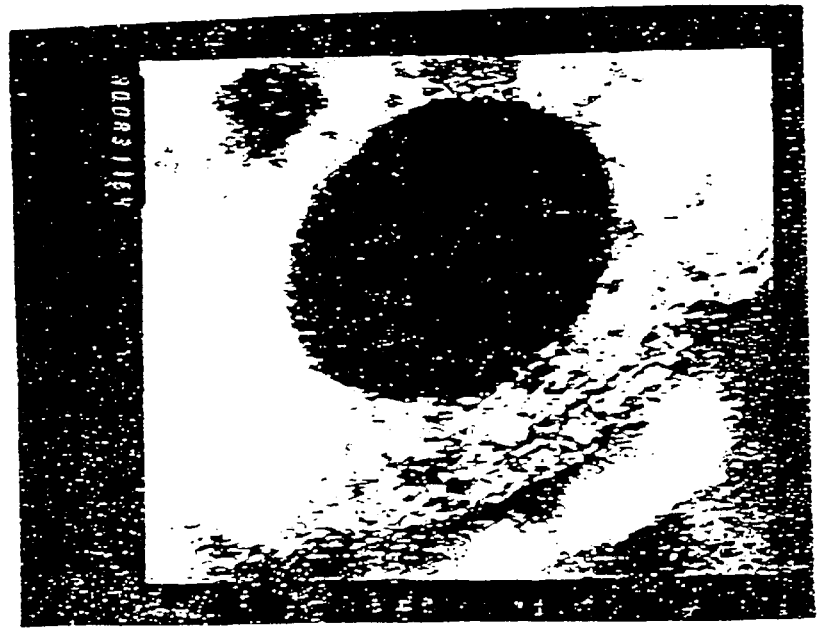
Figure 4, contd

GRAM NEGATIVE COCCOID BACTERIUM *OKADAELLA GASTROCOCCUS*

TECHNICAL FIELD

The present invention relates to an isolated bacterium and uses of the bacterium to diagnose gastrointestinal diseases caused by the bacterium.

BACKGROUND ART

Gastrointestinal disease is a common affliction in animals and humans. Although many aetiological agents including viruses, bacteria and protozoa, have been recognised to cause this disease, there are still many clinical cases from which no causative agent can be identified. Furthermore, many cases do not respond to standard medical treatment regimes suggesting that some unknown agent or agents may be involved.

There have been several new microorganisms identified recently that have been shown to cause gastrointestinal disease in animals including humans. In 1984, Marshall and Warren (Lancet 1984: 1312–1314) described Campylobacter-like, spiral, Gram negative bacteria 2.5 $\mu$m in length and 0.5 $\mu$m in diameter in patients with gastritis and peptic ulcers, now known as *Helicobacter pylori*. In 1987, Dent et al (Lancet 1987 ii:96) reported a new Gram negative spiral bacterium, 3.5–7.5 $\mu$m in length and 0.9 $\mu$m in diameter in patients with gastritis and named it as *Gastrospirillum hominis*. This organism is now called *Helicobacter helimanii*.

The present inventor has isolated and identified a new bacterium that is implicated in gastrointestinal disease in humans.

DISCLOSURE OF INVENTION

A new coccoid form of bacterium, distinct from the coccoid form of *Helicobacter pylori*, which can colonise the human stomach was identified and isolated from a patient with dyspeptic symptoms and found to suffer from a diffused gastritis associated with an erosive gastroduodenitis and multiple superficial ulcerations. The bacterium was resistant to usual triple antibiotic therapy composed of tetracycline, metronidazole, and an $H_2$ antagonist. Symptomatic remission and histological and electron microscopic resolution of the gastro-duodenalpathology following a proton pump inhibitor suggests possible role in the pathogenesis of erosive gastro-duodenitis and multiple superficial ulcerations. The organism is coccoid form and varying in size 0.2–0.75 $\mu$m in diameter, most being 0.3–0.5 $\mu$m in diameter, with outer membrane pilli. The bacterium has been named by the present inventors as *Okadaella gastrococcus* Gen. nov, Sp. nov.

In a first aspect, the present invention consists in an isolated bacterium capable of causing gastrointestinal disease in an animal and having the characteristics of *Okadaella gastrococcus* as herein defined.

Preferably, the bacterium has the following characteristics:

Gram negative;

coccoid;

culturable under microaerophilic and anaerobic conditions;

urease-negative under culture for 2 weeks;

catalase-negative;

oxidase-negative;

contains flagella and may contain microfilamentous hair-like pilli;

bacterial colonies do not fluoresce under ultraviolet light (360 nm);

colonies observed as numerous round "dots" in the Warthin-Starry silver strain; and non *Helicobacter pylori* and non *Helicobacter helimanii*.

A sample of *Okadaella gastrococcus* was deposited under the provisions of the Budapest Treaty with the Australian Government Analytical Laboratories (AGAL) on Sep. 22, 1998 and given Accession Number NM 98/08610.

In a second aspect, the present invention consists in a method of diagnosing gastrointestinal disease in an animal caused by *Okadaella gastrococcus*, the method comprising identifying the presence of the bacterium according to the first aspect of the present invention in the gastrointestinal tract of, or a clinical specimen from, the animal.

The bacterium may be detected directly by culturing the bacterium from a clinical specimen, identifying the bacterium by microscopy, or may be identified indirectly by the use of antibodies to the bacterium. The clinical specimen may be a biopsy, stool specimen, blood sample, or the like. It will be appreciated that the discovery of the bacterium and its association with gastrointestinal disease will allow its detection by any of the known methods of the art. It will also be appreciated that molecular detection methods like polymerase chain reaction (PCR) can also be used to identify the presence of the bacterium in a clinical specimen.

The presence of the bacterium in an animal that does not have clinical signs of gastrointestinal disease may also be indicative of pre-disposition of that animal to gastrointestinal disease. Therefore, the scope of the second aspect of the present invention also includes screening for the presence of the bacterium in animals as a means of detecting animals that may be susceptible to gastrointestinal disease caused by this bacterium.

Preferably, the animal is a human.

In a third aspect, the present invention consists in use of the bacterium according to the first aspect of the present invention to develop diagnostic tools or aids for the detection or diagnosis of disease caused by the bacterium. Such diagnostic tools or aids include molecular probes devised from the genome of the bacterium and antibodies.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers, or steps.

In order that the present invention may be more clearly understood, preferred forms will be described with reference to the accompanying drawings.

DESCRIPTION OF THE INVENTION

Figure 1:
FIG. 1 is a scanning electron micrograph of gastric biopsy specimen showing the coccoid bacteria in the damaged mucosal layer, with an erythrocyte and leukocyte for size comparison, x2,640. Bar=10 $\mu$m.
Figure 2:
FIG. 2 is an enlargement of the scanning micrograph shown in FIG. 1.
Figure 3:
FIG. 3 is a negative stain electron micrograph of the coccoid bacteria, x37,500. Barp=1 $\mu$m.
Figure 4:
FIG. 4 shows transmission electron micrographs of the bacterium according to the present invention.
Figure 4:

In 1983 Warren and Marshall described Campylobacter-like, Gram negative, S-shaped bacilli 2.5 $\mu$m in length and 0.5 μm in diameter in patients with gastritis and peptic ulcers, now known as *Helicobacter pylori*. In 1987, Dent et al reported gram negative spiral bacteria, 3.5–7.5 μm in length and 0.9 μm in diameter in patients with gastritis and named it *Gastrospirillum hominis*, now called *Helicobacter helimannii*.

There is no published information available regarding the identification and isolation of other microorganisms from patients with dyspepsia, even though dyspepsia is one of the most common medical complaints in the World. The present inventors have been attempting to culture, isolate and identify new microorganisms from patients with dyspepsia. A case of a young Japanese who suffers from an erosive gastro-duodenitis with multiple superficial ulcerations with unknown aetiology. The present inventors succeeded to isolate a coccoid form of organism which is not *H. pylori* from this patient. Chan et al reported that the presence of coccoid forms of *H. pylori* is the dominant feature of adenocarcinoma of the stomach. However, international conflicts exist whether the coccoid form of *H. pylori* is a viable dormant form or nonviable degenerative form of the curvilinear microorganism. Therefore, it is very important to distinguish the coccoid form of the microorganism from Helicobacter species which could colonise human gastrointestinal tract. The endoscopic, microbiological, histological and ultrastructural and molecular biological findings of the new micro-organism is provided below.

Case Report

A 20 year old man presented with dyspepsia, indigestion, heartburn and occasional history of gastro-oesophageal reflux. He complained of pre- and post-prandial pain which was relieved by occasional "burping". He denied abdominal bloating, nausea, or vomiting. He also denied a history of melena or recent changes in his bowel habit, except that he suffered from diarrhoea 3–4 times/day around the time when he was found to have duodenitis and multiple duodenal erosion and superficial ulcerations. He denied the use of NSAIDs, his smoking habit was 3–10 cigarettes/day and drinking habit was 375 ml beer per day until this episode. Family history was negative for peptic ulcer disease and gastro-intestinal malignancy. As his condition did not respond to daily treatment with a $H_2$ antagonist for a month, and his *H. pylori* serology test (HEL-pTEST™ II, AMRAD) was positive, he underwent a videoscope endoscopic examination (Olympus GIF XQ 230) and biopsy. As the routine procedure, at least 6–10 biopsy specimens were collected from gastric body and antrum for histological and microbiolgoical examinations. The biopsy specimens and gastric aspirates were cultured under a microaerophilic and anaerobic conditions at 35° C. The biopsy specimens were tested for urease production in a Christensen's urea broth and examined under a microscope with Gram stain. Although the histological and microbiological examination did not reveal the presence of Helicobacter-like microorganisms, he was treated with two weeks course of the triple combination therapy with tetracycline 1.5 g, metronidazole 600 mg and ranitidine 300 mg in divided dose daily (causing greater than 98% successful eradication of *H. pylori*). Further follow-up endoscopic examinations were performed. In all occasions, the endoscopic appearance of the stomach was a generalised gastritis with numerous gastric erosions and multiple surface ulcerations. An erosive duodenitis and multiple surface ulcerations were also seen at the same time. In all occasions, specimens collected from the gastric body and antrum were submitted for histological examination in which were all showed an erosive gastritis with focal superficial ulcerations and focally increased numbers of neutrophils and chronic inflammatory cells in the lamina propria. The aetiology of the gastro-duodenopathy could not be identified by the histological examination. Some epithelial regeneration was seen only in the specimen collected at the time of the third endoscopic examination following one month treatment with omeprasole 20 mg b.d. Therefore, he was treated with omeprasole 20 b.d for 4 months and the fourth endoscopic examination was performed. The endoscopic appearance was hyperaemic erythematous and congested gastric body and antrum and duodenum without gastro-duodenal erosion and ulcerations. The histological examination revealed complete resolution of the erosive gastro-duodenitis and multiple superficial ulcerations. The scanning electron microscopic examination identified some-what enlarged and swollen scattered single coccoid microorganisms in some areas on the surface of gastric epithelium. There were no electron microscopically identifiable surface erosion nor ulceration in the stomach nor duodenum. Adequately regenerated microvilli were observed in the stomach and duodenum. While examining the Gram stained specimen, the present inventors noted Gram negative coccoid bacteria and succeeded to culture the microorganism. The presence of the coccoid organism in the gastric aspirates was also confirmed by the microbiolgoical and electron microscopic examinations. The scanning and transmission electron microscopic examinations identified abundant coccoid forms of bacteria beneath the gastric mucous layer, on the gastric epithelial cells and the clusters of coccoid forms of bacteria in the erosive lesion of the gastric mucosa and in the superficial ulcers. The characteristics of the cultured organism were studied following Gram (G) staining. Haematoxylin and eosin (H&E) stain and Warthin-Starry silver (WSS) stain before subjecting to reviewing all the histological specimens. The bacteria were difficult to see in H&E stained histological sections. When they could see, the microorganism was recognised as a basophilic clustered mass. The organism was observed as a numerous round "dots" in the WSS. The bacteria were abundant in the superficial layer of the gastric mucosa, and could be identified in the erosive lesion of the gastric mucosa and gastric pits. The organism was urease-, catalase-, and oxidase-negative. They converted arginine-β-naphthylamine to arginine. This suggested that the organism possessed arginine aminopeptidase. The mature bacterium possessed unique flagella and were surrounded by fine microfilamentous hair-like pilli. These structures may not be identified in all cases. The 16S rRNA sequencing study confirmed that the coccoid form of bacteria were not phylogenically related with the coccid form of *H. pylori* but were closer to *Haemophilus haemolyticus*. DNA comparison studies of the coccoid form and *H. haemolyticus* demonstrated that the microorganisms are different. The response to factor X and V which are required to determine the genus Haemophilus were also tested with the results being negative for both. The growth conditions and environment of Haemophilus are not suitable for the coccoid form of the organism. The growth rate was totally different from Haemophilus which growth can be detected after 24 hours incubation. The coccid organism, however, takes at least 7 days to give any hint of colony formation. The colony appearance and morphology are also different. The biochemical test results were totally different from Haemophilus and could not identified by the commercially available identification kit, Neisseria/Haemophilus identification card (biomerieux, Vitek), nor by RapID ANA II system (Innovative Diagnostic Systems) for identification of anaerobic organism. Chocolate agar was used as the standard for culturing Haemophilus, which is not optimal for the new organism.

Immunoperoxidase stain study was performed on a paraffin block section to exclude the possibility of coccoid forms of *H. pylori* colonisation. There was no *H. pylori* sera reaction identified.

Discussion

The microaerophilic and anaerobic gram-negative coccoid form of bacteria which colonised the human stomach mucosa have not been cultured previously, and their association with an erosive gastro-duodenitis and multiple superficial ulcerations have not been described. The main reason why the new bacteria could not have been detected previously is probably due to their size and appearance which resemble to cell debris such as cytoplasmic granules in particular expelled chromatins from cell nuclei on inflamed, erosive and ulcerated gastric mucosal cells. The organism may have been seen but regarded as oropharygeal contaminants, or superseded by the presence of *H. pylori* and regarded as commensals. The possibility also exists that the bacteria were misinterpreted and thought as the coccoid form of *H. pylori*. At first, it was very difficult to detect the presence of the organism in histological specimens even by very well trained and experienced pathologists until the size, nature and characteristics of the isolated organism which were stained with G, H&E and WSS was recognised. Second, it is quite easy to discard and neglect the cultured colonies as they are very small and about 0.5–1 mm in diameter after about 1 week incubation. The Gram stained cultured specimen often appears like a Gram negative artefact rather than clear distinct microorganism as they are densely packed and clustered bacteria and appear like "sand". The other reason could have been due to the neglect of gastric microbiology and the concept that the stomach is a sterile organ as stated by Warren when he identified S-shaped bacilli patients with gastritis.

It is important to make an accurate diagnosis of the gastro-duodenal pathology if it is associated with bacterial colonisation like *H. pylori, H. helimannii*, Okadaell infection (Okada et al 1998) or other bacterial infections; candida (Ralogeropoulos et al 1988), cryptosporidium (Cersosimo et al 1992), as the treatment choice would be different. One may select triple therapy incorporating tetracycline and metronidazole which achieves a significantly higher successful eradication of *H. pylori* than others (Chiba et al 1992). Okadaella gastrococci were resistant to the combination treatment with ranitidine, tetracycline and metronidazole for 2 weeks. Considering the disappearance of the organism histologically and microbiologically following 4 months treatment with omeprazole coincided with histological and symptomatic improvement of this patient, the combination therapy with proton pump inhibitors could produce greater efficacy than other classes of acid-suppressing agents in the management of an erosive gastro-duodenitis and peptic ulcer disease due to Helicobacter and Okadaella infection.

The organism isolated by the present inventors does not fit into known genus Haemophilus, judging from the colony, cell morphology, growth characteristics, antibiotic susceptibility, biochemical tests, and DNA analysis although the new organism has close phylogenic relationships with *H. haemolyticus*. The genus called Okadaella Gen. nov. (Oka. da.-ella: Jap. n. Okada; N. L. masc. n. Okadella, named after Dr T Okada who identified the bacterium), *gastrococcus* Sp. *nov.* (Gr.n. gastr: pertaining to the stomach; Gr. n. coccus: grain) is proposed for the present microorganism. Antibodies raised against this organism and performance of immuno-histo-fluorescence and indirect immuno-histochemical studies will be useful to show that the bacteria isolated are identical to the organisms on the surface of the gastric mucosal epithelium. In addition, DNA hybridisation studies with the genus Haemophilus can be carried out to develop reliable rapid detecting methods for Okadaella species utilising PCR and reverse transcription probes for known 16S rRNA and DNA sequences of arginine aminopeptidase, for example.

Biochemical Characteristics of *Okadaella gastrococcus*

Growth medium—Horse blood agar (eg. Colombia agar)

Optimal growth condition: 35–37° C.

Growth condition: Microseropilic and anaerobic $CO_2$: 10%, $O_2$:4 86%, $N_2$: 85.14%)

Colony size to reach 0.5–1.0 mm: 7–14 days

Colony morphology: Convex, smooth, translucent

Cell body diameter: 0.3–5 μm

Cell body length: 0.2–0.75 μm

Mole % G+C: not determined

X factor requirement: No

Y factor requirement: No

Catalase: negative

Oxidase: negative

Urease: negative

Indole: negative

Ornithine decarboxylase: negative

Haemolysis: negative

Alkaline-phosphatase: not determined

Glucose: negative

Acid production from
L-arabinose: negative
D-galactose: negative
Maltose: negative
Sucrose: negative Galactosidase(ONPG): negative (ONPG: o-nitrophenyl-D-galactosidase)

Frucosidase: negative

Glucosidase: negative

Arginine aminopeptidase: Positive

Nitrate reduction: negative

Nitrite reduction: negative $H_2S$ production: not determined

G-Glutamyl transpeptidase: not determined

Storage at −70° C. with horse red blood cells or horse serum.

(Positive: 90% or more of strains are positive)

(Negative: 10% or less of strains are positive)

References

Noach L. A., Rolf T. M., Mytgat G. N. Electron microscopic study of association between *Helicobacter pylori* and gastric and duodenal mucosa, J. Clin Pathol 1994:47:699–704

Ogata T. and Araki K. Electron microscopic study of the morphological changes of gastric mucous cell induced by *Helicobacter pylori* in human gastric ulcers, J. Submicros Pathol T, 28 (2) 255–264, 1996.

Bode G., Malfertheiner P. and Ditschuneit H. Pathogenic implications of ultrastructural findings in *Campylobacter pylori* related gastroduodenal disease Scand J Gastroenterol 1998, 23 (suppl 142), 25–39.

It will be appreciated by persons skilled in the art that numerous variations and/or modifications may be made to the invention as shown in the specific embodiments without departing from the spirit or scope of the invention as already described. The present embodiments are, therefore, to be considered in all respects as illustrative and not restrictive.

Biochemical characteristics of Okadaella (O) and Haemophilus (H) organisms
Gc, gastrococcus; GE, gastrofilamenti; inf, influenzae; par, parainfluenzae; haem, haemolyticus

| Characteristics | OGc | OGf | H. inf | H. par | H. haem | HP |
|---|---|---|---|---|---|---|
| G. medium | H.B.A. | H.B.A. | C.A. | C.A. | C.A. | H.B.A. |
| Optimal G. temp | 35–37 | 35–37 | 35–37 | 35–37 | 35–37 | 35–37 |
| G condition | MA&An | MA&An | A/FAn | A/FAn | A/FAn | MA&An |
| Colony size to reach 0.5–1.0 mm | 7–14 days | 7–14 days | 24 hrs | 24 hrs | 24 hrs | 3–4 days |
| Colony morph. | convex TL smooth | convex TL smooth | convex G/TL smooth | convex G/Y smooth | convex TL smooth | convex TL smooth |
| Cell diameter um | 0.3–0.5 | 0.5 | 0.3–0.5 | | | 0.5 |
| Cell length um | 0.2–0.75 | >20 | 0.5–3.0 | | | 2.5–4.0 |
| Mole % G + C (Tm) | ? | ? | 37–44 | 40.41 | 39 | 35–44 |
| Xfactor requirement | No | (No) | Yes | Yes | Yes | No |
| Vfactor requirement | No | No | Yes | No | Yes | No |
| Catalase | − | (−) | + | +/d | + | + |
| Oxidase | − | (−) | + | + | + | + |
| Urease | − | (−) | +/− | +/− | + | + |
| Indole | − | (−) | +/− | − | d | − |
| Ornithine decarboxy | − | (−) | +/− | +/− | − | ? |
| Hemolysis | − | (−) | − | − | + | − |
| Alkaline phosphatase | ? | ? | + | + | + | + |
| AMP reaction | | | | | | |
| Glucose | − | (−) | + | + | + | ? |
| Acid production from | | | | | | |
| L-Arabinose | − | (−) | − | − | − | ? |
| D-Galactose | − | (−) | + | + | + | |
| Maltose | − | (−) | + | + | + | |
| Sucrose | − | (−) | − | + | − | |
| -Galactosidase (ONPG) | − | (−) | − | +/d | − | |
| -Fucosidase | − | (−) | − | − | − | |
| -Glucosidase | − | (−) | −? | − | − | |
| -Glucosidase | − | (−) | − | − | − | |
| Arginine aminopeptidase | + | (+) | − | − | − | |
| Nitrate reduction | − | (−) | + | + | + | − |
| Nitrate reduction | − | (−) | − | + | d | |
| H$_2$S production | ? | ? | − | + | + | − |

+, 90% or more of strains are positive; d, 11–89% of strains are positive. ONPG, o-nitrophenyl- -Dgalactoside.H.B.A., horse blood agar; CA, chocolate agar. MA&A, microaerophilic and anaerobic condition; A/FAn, aerobic/facultatively anaerobic.

What is claimed is:

1. An isolated bacterium capable of causing gastrointestinal disease in an animal and having the characteristics of *Okadaella gastrococcus*.

2. The bacterium according to claim 1 being *Okadaella gastrococcus*.

3. The bacterium according to claim 2 having Accession Number NM 98/08610.

4. The bacterium according to claim 1 having the following characteristics:
   Gram negative;
   coccoid;
   culturable under microaerophilic and anaerobic conditions;
   urease-negative under culture for 2 weeks;
   catalase-negative;
   oxidase-negative;
   contains flagella and may contain microfilamentous hair-like pilli;
   bacterial colonies do not fluoresce under ultraviolet light (360 nm); and
   colonies observed as numerous round "dots" in the Warthin-Starry silver strain.

5. A method of diagnosing gastrointestinal disease in an animal caused by the bacterium *Okadaella gastrococcus*, the method comprising detecting the presence of said bacterium in the gastrointestinal tract of, or in a clinical specimen from, the animal.

6. The method according to claim 5 wherein the bacterium is detected directly by culturing the bacterium from a clinical specimen, identifying the bacterium by microscopy; or identified indirectly by the use of antibodies to the bacterium, or amplification or detection of unique portions of the bacterium genome.

7. The method according to claim 6 wherein the clinical specimen is a biopsy, stool specimen, or blood sample.

8. The method according to claim 5 wherein the animal is a human.

9. A diagnostic tool for detection of disease caused by a bacterium having the characteristics of *Okadaella gastrococcus* comprising said bacterium having the characteristics of *Okadaella gastrococcus*.

* * * * *